United States Patent
Jang et al.

(10) Patent No.: US 10,890,675 B2
(45) Date of Patent: Jan. 12, 2021

(54) SYSTEM FOR PROCESSING BEAM POSITION MONITOR SIGNAL

(71) Applicant: Korea University Research and Business Foundation, Sejong Campus, Sejong-si (KR)

(72) Inventors: Siwon Jang, Sejong-si (KR); Eun-San Kim, Sejong-si (KR)

(73) Assignee: KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 197 days.

(21) Appl. No.: 16/146,277

(22) Filed: Sep. 28, 2018

(65) Prior Publication Data

US 2019/0094395 A1    Mar. 28, 2019

(30) Foreign Application Priority Data

Sep. 28, 2017  (KR) .......................... 10-2017-0125861

(51) Int. Cl.
   *G01T 1/29*      (2006.01)
   *G01T 1/17*      (2006.01)
   *A61N 5/10*      (2006.01)

(52) U.S. Cl.
   CPC .............. *G01T 1/2921* (2013.01); *G01T 1/17* (2013.01); *G01T 1/29* (2013.01); *A61N 5/1075* (2013.01); *A61N 2005/1087* (2013.01)

(58) Field of Classification Search
   CPC . A61N 2005/1087; A61N 5/1075; H05H 7/22
   See application file for complete search history.

(56) References Cited

U.S. PATENT DOCUMENTS

| | | | | |
|---|---|---|---|---|
| 5,459,393 | A * | 10/1995 | Tanaka | G01T 1/29 315/500 |
| 2003/0183779 | A1* | 10/2003 | Norimine | H05H 7/04 250/492.3 |
| 2007/0295910 | A1* | 12/2007 | Harada | G21K 5/04 250/354.1 |

(Continued)

OTHER PUBLICATIONS

S. Jang et al., The Development of Button Type BPM Electronics for RAON; Proceedings of IPAC2017, May 19, 2017, pp. 362-364, Cophenhagen, Denmark.

(Continued)

*Primary Examiner* — Dani Fox
*Assistant Examiner* — Soorena Kefayati
(74) *Attorney, Agent, or Firm* — Hauptman Ham, LLP

(57) ABSTRACT

Provided are a system and method for processing a beam position monitor signal using an analog-to-digital converter (ADC) sampler corresponding to an analog part and an FPGA corresponding to a digital signal processing part. The ADC sampler measures signal intensity through an optimization of an ADC sampling rate and bits using a radio frequency (RF) switch and a low noise amplifier (LNA), and converts an analog signal into a digital signal. The FPGA extracts only an optimized harmonic signal among multiple harmonic signals of the digital signal converted by the ADC sampler, through a digital band pass filter; and performs beam position measurement, beam phase measurement and relative beam current measurement on the extracted digital signal through a digital circuit.

9 Claims, 9 Drawing Sheets

(56) References Cited

U.S. PATENT DOCUMENTS

| | | | | |
|---|---|---|---|---|
| 2009/0039256 A1* | 2/2009 | Fujii | A61N 5/1048 | 250/306 |
| 2010/0012829 A1* | 1/2010 | Islam | G01T 1/185 | 250/252.1 |
| 2010/0219350 A1* | 9/2010 | Kobashi | C23C 16/0254 | 250/370.1 |
| 2011/0186746 A1* | 8/2011 | Drees | A61N 5/10 | 250/397 |
| 2011/0248188 A1* | 10/2011 | Brusasco | A61N 5/1048 | 250/492.1 |
| 2011/0260074 A1* | 10/2011 | Honda | A61N 5/1043 | 250/396 R |
| 2012/0001085 A1* | 1/2012 | Fujimoto | A61N 5/103 | 250/396 ML |
| 2012/0056098 A1* | 3/2012 | Harada | G21K 1/093 | 250/396 R |
| 2012/0185208 A1* | 7/2012 | Baricevic | H05H 7/00 | 702/150 |
| 2012/0215495 A1* | 8/2012 | Yamaguchi | G01T 1/29 | 702/189 |
| 2012/0223247 A1* | 9/2012 | Honda | A61N 5/1043 | 250/396 R |
| 2012/0262333 A1* | 10/2012 | Trummer | H05H 7/22 | 342/146 |
| 2012/0305796 A1* | 12/2012 | Iseki | A61N 5/10 | 250/396 R |
| 2013/0113503 A1* | 5/2013 | Ruf | G01T 1/29 | 324/654 |
| 2013/0190548 A1* | 7/2013 | Honda | G01T 1/29 | 600/1 |
| 2013/0231517 A1* | 9/2013 | Iwamoto | A61N 5/1043 | 600/1 |
| 2014/0031602 A1* | 1/2014 | Fujimoto | A61N 5/1037 | 600/1 |
| 2014/0061498 A1* | 3/2014 | Honda | A61N 5/1075 | 250/397 |
| 2014/0166896 A1* | 6/2014 | Bert | H01J 37/304 | 250/397 |
| 2014/0265823 A1* | 9/2014 | Boisseau | A61N 5/1075 | 313/545 |
| 2015/0041665 A1* | 2/2015 | Hollebeek | G01T 1/2935 | 250/375 |
| 2015/0131780 A1* | 5/2015 | Tsunoo | A61B 5/0873 | 378/62 |
| 2015/0238780 A1* | 8/2015 | Nishimura | A61N 5/1075 | 600/2 |
| 2015/0313001 A1* | 10/2015 | Harasimowicz | H05H 9/048 | 315/505 |
| 2016/0030769 A1* | 2/2016 | Cameron | A61N 5/1043 | 600/1 |
| 2016/0144202 A1* | 5/2016 | Hanakawa | H05H 7/04 | 600/1 |
| 2016/0150630 A1* | 5/2016 | Tsubuku | A61N 5/1068 | 600/1 |
| 2016/0213950 A1* | 7/2016 | Ebina | A61N 5/1077 | |
| 2017/0112457 A1* | 4/2017 | Allinson | A61N 5/1077 | |

OTHER PUBLICATIONS

Korean Office Action dated Dec. 17, 2018 in connection with the counterpart Korean Patent Application No. 10-2017-0125861, citing the above reference(s).

* cited by examiner

SYSTEM FOR PROCESSING BEAM POSITION MONITOR SIGNAL

CROSS REFERENCE TO RELATED APPLICATION

The present application claims the benefit of Korean Patent Application No. 10-2017-0125861 filed in the Korean Intellectual Property Office on Sep. 28, 2017 the entire contents of which are incorporated herein by reference.

BACKGROUND OF THE INVENTION

1. Technical Field

The present invention relates to an accelerator diagnostic apparatus and, more particularly, to a method and system for processing a signal of a beam position monitor for a heavy ion accelerator.

2. Description of the Related Art

U.S. Patent No. 2012/0262333 A1 entitled "BEAM POSITION MONITOR FOR ELECTRON LINEAR ACCELERATOR" is a conventional technology in the technical field to which the present invention belongs, and discloses a beam position monitor for an electron linear accelerator and electronics that is an apparatus for signal processing. Specifically, a method of separating the electronics into an analog part and a digital part and processing a signal is the background of the present invention.

The conventional technology discloses a device in which the analog circuit performs signal synthesis, generates an IQ (position and phase) signal, and analyzes the signal and an electron beam is a target. In this case, beam position measurement for each multi-harmonic signal is impossible. Furthermore, in an operating mode of a heavy ion accelerator in which a bunch repetition rate is several tens of MHz, beam position measurement for a micro bunch is impossible.

Accordingly, there is a need for a method and system capable of measuring a variety of types of heavy ion beams and measuring the phase component of a beam in addition to the position of the beam.

SUMMARY OF THE INVENTION

An object of the present invention is to provide a method and system which can be applied to various heavy ion operating modes of a heavy ion accelerator using an analog RF circuit and a digital circuit.

In one aspect, a system for processing a signal of a beam position monitor proposed in the present invention includes an analog-to-digital converter (ADC) sampler configured to measure signal intensity through the optimization of an ADC sampling rate and bits using a radio frequency (RF) switch and a low noise amplifier (LNA) and to convert an analog signal into a digital signal and an FPGA configured to perform digital signal processing. The FPGA is further configured to include a digital signal synthesizer configured to extract only an optimized harmonic signal of multiple harmonic signals of the digital signal converted by the ADC sampler through a digital band pass filter so that the multiple harmonic signals are separated and signal processing is performed for each harmonics, and an IQ calculator configured to perform beam position measurement, beam position measurement and relative beam current measurement on the extracted digital signal through a digital circuit.

The ADC sampler is further configured to include the LNA configured to receive a pick-up RF signal and a reference RF signal and to amplify a monitor signal and a low pass filter (LPF) configured to filter out the noise of the RF signal.

The ADC sampler is further configured to expand a measurable range of signal intensity using the RF switch and the LNA and to reduce a measureable interval of a beam position signal of a pulse length using a high-speed ADC sampling frequency of 105 MHz or more.

The digital signal synthesizer is further configured to include an averaging unit configured to perform averaging on a given interval of the digital signal converted by the ADC sampler, an A/P calculator configured to translate or inversely translate a size and phase using an IQ value calculated by an IQ calculator, and an FFT/filtering unit configured to perform high-speed Fourier transform or filtering.

The digital signal synthesizer is further configured to perform signal processing using a 1st harmonic signal of a predetermined frequency and a $3^{rd}$ harmonic signal of a predetermined frequency for a signal of a high-beta interval.

In another aspect, a method of processing a signal of a beam position monitor proposed in the present invention includes measuring signal intensity through the optimization of an ADC sampling rate and bits using a radio frequency (RF) switch and a low noise amplifier (LNA) and converting an analog signal into a digital signal, extracting only an optimized harmonic signal of multiple harmonic signals of the digital signal converted by an analog-to-digital converter (ADC) sampler using a digital band pass filter so that the multiple harmonic signals are separated and signal processing is performed for each harmonics, and performing beam position measurement, beam position measurement and relative beam current measurement on the extracted digital signal through a digital circuit.

measuring signal intensity through the optimization of an ADC sampling rate and bits using a radio frequency (RF) switch and a low noise amplifier (LNA) and converting an analog signal into a digital signal includes receiving a pick-up RF signal and a reference RF signal, amplifying a monitor signal through the LNA, and filtering out noise of the RF signal through a low pass filter (LPF). In this case, a measurable range of signal intensity is expanded using the RF switch and the LNA, and a measureable interval of a beam position signal of a pulse length is reduced using a high-speed ADC sampling frequency of 105 MHz or more.

Extracting only an optimized harmonic signal of multiple harmonic signals of the digital signal converted by an analog-to-digital converter (ADC) sampler using a digital band pass filter so that the multiple harmonic signals are separated and signal processing is performed for each harmonics includes performing, by an averaging unit, averaging on a given interval of the digital signal converted by the ADC sampler, translating or inversely translating, by an A/P calculator, a size and phase using an IQ value calculated by an IQ calculator, and performing, by an FFT/filtering unit, high-speed Fourier transform or filtering. In this case, signal processing is performed using a $1^{st}$ harmonic signal of a predetermined frequency and a $3^{rd}$ harmonic signal of a predetermined frequency for a signal of a high-beta interval.

DETAILED DESCRIPTION

In the conventional technology, the analog circuit performs signal synthesis, generates an IQ (position and phase) signal, and analyzes the signal. In contrast, in an embodiment of the present invention, the position and phase component of a beam can be measured using a digital IQ signal processing method through signal synthetic using a digital circuit and the optimization of an analog-to-digital converter (ADC) sampling rate (i.e., sampling rate). Furthermore, the target of the conventional technology is an electron beam. In contrast, the system for processing a signal of a beam position monitor according to an embodiment of the present invention has been developed to measure a variety of types of heavy ion beams.

In the conventional technology, the analog part mixes signals and converts a radio frequency (RF) signal into a frequency of a base band. In this case, beam position measurement for each multi-harmonic signal is impossible. Furthermore, in an operating mode of a heavy ion accelerator in which a bunch repetition rate is several tens of MHz, the present invention has developed electronics so that it can be applied to various heavy ion operating modes of the heavy ion accelerator using an analog RF circuit and a digital circuit in order to enable beam position measurement of a micro bunch. Hereinafter, embodiments of the present invention are described in detail with reference to the accompanying drawings.

Figure 1:
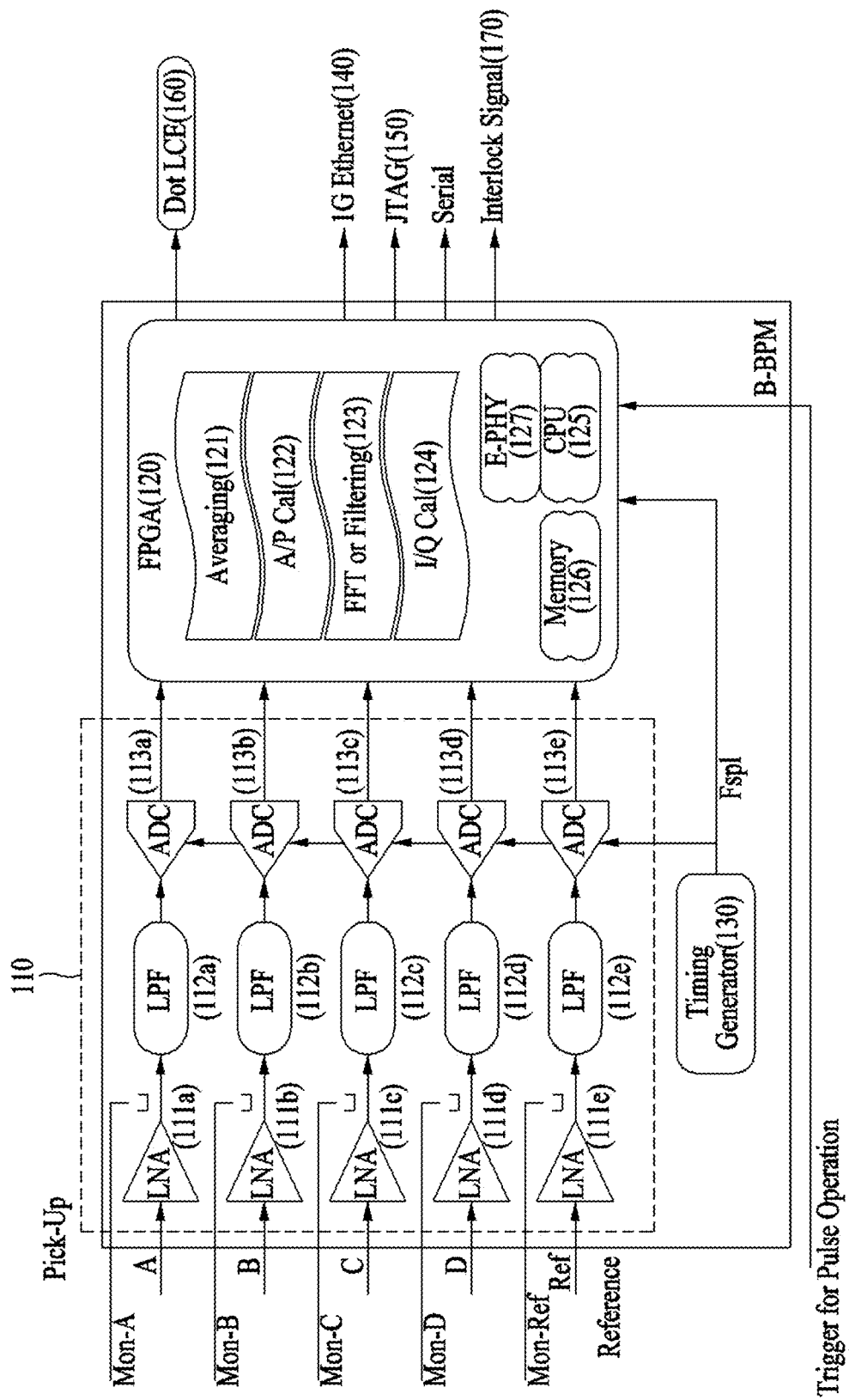
FIG. 1 is a diagram showing the configuration of a system for processing a signal of a beam position monitor according to an embodiment of the present invention.

FIG. 1 is a diagram showing the configuration of a system for processing a signal of a beam position monitor according to an embodiment of the present invention.

Unlike in the conventional technology, in the system for processing a signal of a beam position monitor according to an embodiment of the present invention, in order to process a signal of a very short pulse occurring in the beam position monitor, the digital part has been more improved than the analog part and invented for a button type beam position monitor of a heavy ion accelerator. First, the heavy ion accelerator has a very wide range (10 nA~mA) of a measurable beam current because it has to accelerate a variety of types of nuclei. This means that the measurable range of electronics to measure a beam position signal needs to be very wide.

To this end, first, the electronics according to an embodiment of the present invention is designed to measure signal intensity of a very wide range using an RF switch and a dual low noise amplifier (LNA) in the analog part.

A BPM signal processor for the signal processing of the beam position monitor basically includes an analog circuit and a digital circuit. The analog circuit includes an amplifier for amplifying a BPM signal and a low pass filter (LPF) for suppressing high order signals and a noise signal.

The digital circuit includes an ADC for converting an analog signal into a digital signal, and may be configured to perform signal processing using a $1^{st}$ harmonic signal of 81.25 MHz and a $3^{rd}$ harmonic signal of 243.75 MHz for a signal of a high-beta interval. A digital signal processing circuit may be configured to perform signal processing using an FPGA and to provide beam position information and beam phase information. Specifically, the present invention includes a circuit capable of precisely calculating precise beam position information and beam phase information through the sampling frequency optimization of the ADC and an IQ calculation method.

Only a beam position is not simply measured, but beam position measurement, beam position measurement and relative beam current measurement, and a role as an assistant device of an accelerator device protection system can be performed using the digital circuit.

A BPM signal sensor according to an embodiment of the present invention is described in detail below.

The proposed system for processing a signal of the beam position monitor includes an ADC sampler 110 configured to measure signal intensity through the optimization of an ADC sampling rate and bits using an RF switch and LNAs 111a, 111b, 111c, 111d and 111e and to convert an analog signal into a digital signal using ADCs 113a, 113b, 111c, 113d and 113e and an FPGA 120 configured to process a digital signal.

The FPGA 120 includes a digital signal synthesizer configured to extract only an optimized harmonic signal of multiple harmonic signals through a digital band pass filter so that the multiple harmonic signals of a digital signal converted through the ADC sampler 110 are separated and signal processing is performed for each harmonics and an IQ calculator 124 configured to perform beam position measurement, beam position measurement and relative beam current measurement on the extracted digital signal through a digital circuit. More specifically, the digital signal synthesizer of the FPGA 120 includes an averaging unit 121, an A/P calculator 122 and an FFT/filtering unit 123.

First, the ADC sampler 110 corresponding to the analog part includes the LNAs 111a, 111b, 111c, 111d and 111e configured to receive a pick-up RF signal and a reference RF signal as inputs and to amplify a monitor signal and LPFs 112a, 112b, 112c, 112d and 112e configured to filter out the noise of an RF signal.

The LNAs 111a, 111b, 111c, 111d and 111e receive a pick-up RF signal and a reference RF signal and amplify them as a gain of 10~20 dB.

The ADCs 113a, 113b, 111c, 113d and 113e according to an embodiment of the present invention have resolution of 16 bits, 200 MSPS and a maximum of 5 channels.

The ADC sampler 110 extends a measurable range of signal intensity using the RF switch and the LNA and reduces the interval of a beam position signal of a measurable pulse length using a high-speed ADC sampling frequency of 105 MHz or more. For example, the ADC sampler 110 is designed to measure a beam position signal of a 1 ns-pulse length at intervals of 1 us using a fast ADC sampling frequency of 105 MHz.

The proposed system for processing a signal of the beam position monitor may further include a timing generator 130, a 1G Ethernet 140, a JTAG/Serial 150, a Dot LCD 160, a CPU 125, memory 126, an E-PHY 127 and an interlock signal 170.

The timing generator 130 generates a timing signal for the system. For example, the timing generator generates a sampling clock (Fspl) and provides an FPGA operation clock.

The 1G Ethernet 140 provides a communication port for operating in conjunction with an external PC, installs an EPICS IOC and CSS program on an external PC, and controls the system.

The JTAG/Serial 150 provides a JTAG port for FPGA development and a serial port for system debugging.

The Dot LCD 160 displays basic information (e.g., NW IP) about the system for use convenience.

The CPU 125 operates in conjunction with an external PC using the DSP operating results of the FPGA of 1 GbE communication, receives a configuration/control command from an external PC, and performs control so that the FPGA is performed.

The Interlock Signal 170 monitors beam position data, and immediately generates an interlock signal when an abnormal situation occurs.

The digital signal synthesizer corresponding to the digital part includes the averaging unit 121, the A/P calculator 122 and the FFT/filtering unit 123.

The averaging unit 121 performs averaging on a given interval of a digital signal converted by the ADC sampler.

The A/P calculator 122 translates or inversely translates a size and phase using an IQ value calculated by the IQ calculator.

The FFT/filtering unit 123 performs high-speed Fourier transform or filtering.

The digital signal synthesizer is configured to separate multiple harmonic signals through digital down conversion and enables signal processing for each harmonics. Thereafter, the digital signal synthesizer is configured to extract only an optimized harmonic signal of multiple harmonic signals, that is, characteristics of the heavy ion accelerator, as a digital band pass filter, and to precisely measure a beam position.

Figure 2:
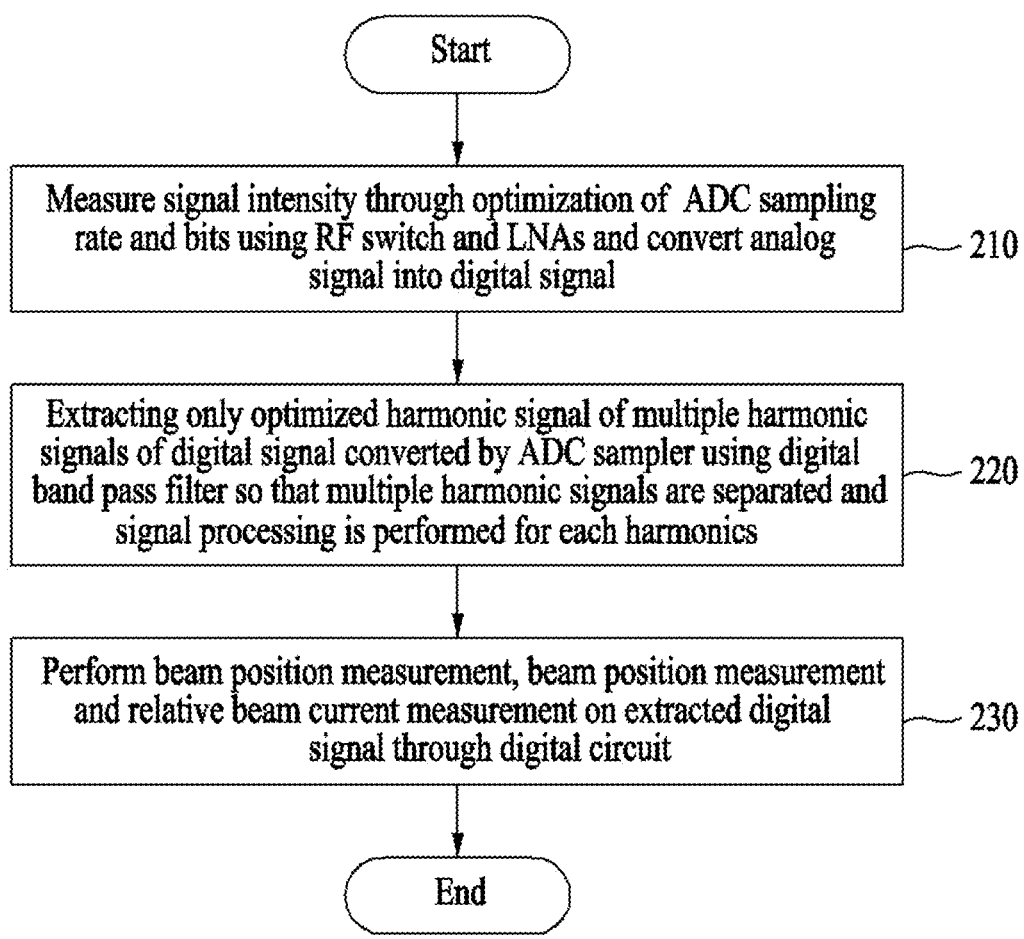
FIG. 2 is a diagram showing a flowchart of a method of processing a signal of a beam position monitor according to an embodiment of the present invention.

FIG. 2 is a diagram showing a flowchart of a method of processing a signal of the beam position monitor according to an embodiment of the present invention.

The BPM signal processor for the signal processing of the beam position monitor basically includes an analog circuit and a digital circuit. The analog circuit includes an amplifier for amplifying a BPM signal and an LPF for suppressing high order signals and a noise signal.

The digital circuit includes an ADC for converting an analog signal into a digital signal. The digital circuit may be configured to perform signal processing using the $1^{st}$ harmonic signal of 81.25 MHz and the $3^{rd}$ harmonic signal of 243.75 MHz for a signal of a high-beta interval. A digital signal processing circuit may be configured to perform signal processing using an FPGA and to provide beam position information and beam phase information. Specifically, the present invention has implemented a circuit capable of precisely calculating beam position information and beam phase information through the sampling frequency optimization of an ADC and an IQ calculation method.

In the present invention, only a beam position is not simply measured, but beam position measurement, beam position measurement and relative beam current measurement, and a role as an assistant device of an accelerator device protection system can be performed using the digital circuit.

The proposed method of processing a signal of the beam position monitor includes the step 210 of measuring signal intensity through the optimization of an ADC sampling rate and bits using the RF switch and the LNAs and converting an analog signal into a digital signal, the step 220 of extracting only an optimized harmonic signal of multiple harmonic signals of the digital signal converted by the ADC sampler using the digital band pass filter so that the multiple harmonic signals are separated and signal processing is performed for each harmonics, and the step 230 of performing beam position measurement, beam position measurement and relative beam current measurement on the extracted digital signal through the digital circuit.

In step 210, signal intensity is measured through the optimization of an ADC sampling rate and bits using the RF switch and the LNA. The analog signal is converted into the digital signal.

In this case, a measurable range of signal intensity is extended using the RF switch and the LNA. The interval of a beam position signal of a measurable pulse length is reduced using a high-speed ADC sampling frequency of 105 MHz or more. For example, a beam position signal of a 1 ns-pulse length may be measured at intervals of 1 us using a fast ADC sampling frequency of 105 MHz.

In step 220, only an optimized harmonic signal of multiple harmonic signals of the digital signal converted by the ADC sampler is extracted through the digital band pass filter so that the multiple harmonic signals are separated and signal processing is performed for each harmonics.

In this case, an averaging of an averaging unit is performed on a given interval of the digital signal converted by the ADC sampler. The A/P calculator translates or inversely translates a size and phase using an IQ value calculated by the IQ calculator. Furthermore, high-speed Fourier transform or filtering is performed through the FFT/filtering unit. Furthermore, signal processing is performed using a $1^{st}$ harmonic signal of a predetermined frequency and a $3^{rd}$ harmonic signal of a predetermined frequency for a signal of a high-beta interval.

In step 230, beam position measurement, beam position measurement and relative beam current measurement are performed on the extracted digital signal using the digital circuit.

Figure 3:
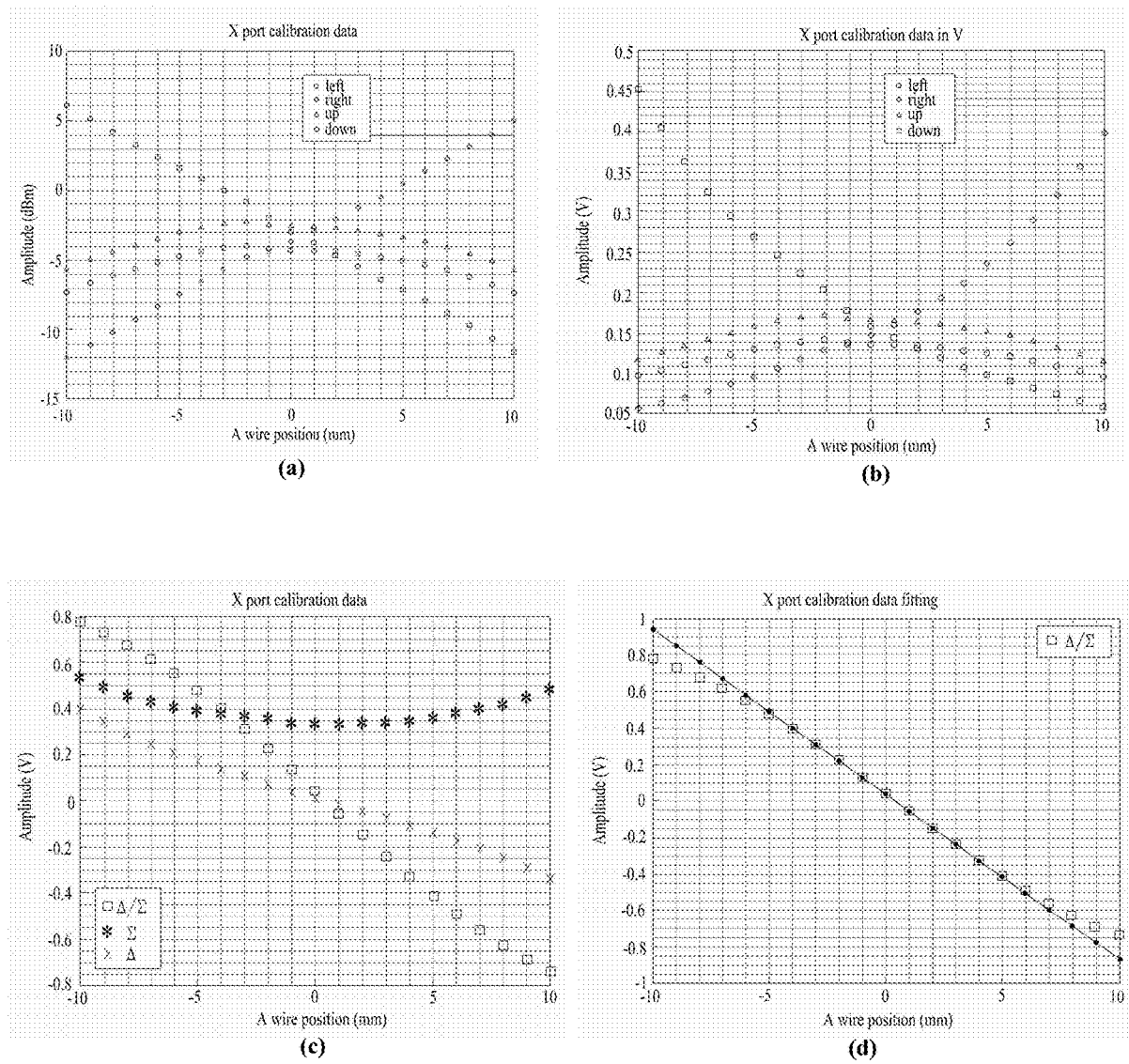
FIG. 3 is a diagram showing X-port calibration results and position measurement results using a $1^{st}$ harmonic signal according to an embodiment of the present invention.

FIG. 3 is a diagram showing X-port calibration results and position measurement results using the $1^{st}$ harmonic signal according to an embodiment of the present invention.

Position resolution of a BPM controller according to an embodiment of the present invention, that is, X-port calibration results and position using the $1^{st}$ harmonic signal, was measured as follows, and measurement results thereof are shown in FIG. 3.

Position resolution measurement of the $1^{st}$ harmonic signal (81.25 MHz)

Measurement was performed based on signal intensity of 100 uA

X-port Calibration slope: −0.0905 V/mm, offset: 0.0367 mm

X-port resolution limit=7.4 um

Figure 4:
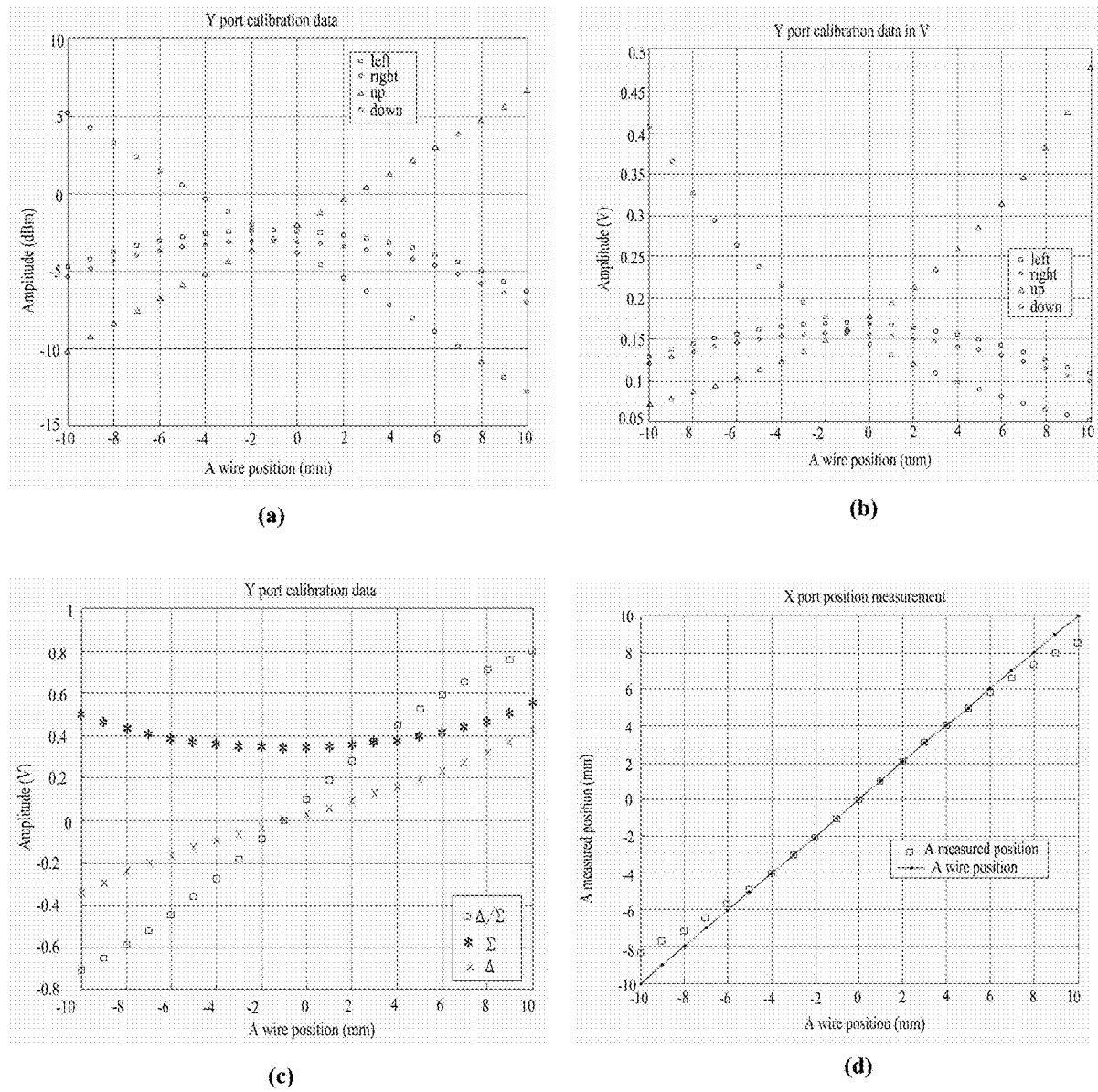
FIG. 4 is a diagram showing Y-port calibration results and position measurement results using a $1^{st}$ harmonic signal according to an embodiment of the present invention.

X-port accuracy with narrow (±5 mm): 35.6 um, accuracy with full (±10 mm): 539.5 um FIG. 4 is a diagram showing Y-port calibration results and position measurement results using the $1^{st}$ harmonic signal according to an embodiment of the present invention.

Y-port calibration results and position using the $1^{st}$ harmonic signal according to an embodiment of the present invention was measured as follows, and measurement results thereof are shown in FIG. 4.

Y-port Calibration slope: 0.0898 V/mm, offset: 0.0920 mm

Y-port resolution limit=7.4 um

Y-port accuracy with narrow (±5 mm): 51.4 um, accuracy with full (±10 mm): 569.2 um The position resolution measurement results were performed 7.4 um in both a horizontal direction and a vertical direction.

In the case of measurement accuracy of the position, measurement was basically performed in two cases. In a linear interval used to calculate a calibration slope, 35.6 um in the horizontal direction and 51.4 um in the vertical direction were measured. In a ±10 mm interval, that is, the entire measurement interval, 539.5 um in the horizontal direction and 569.2 um in the vertical direction were measured as average values.

Figure 5:
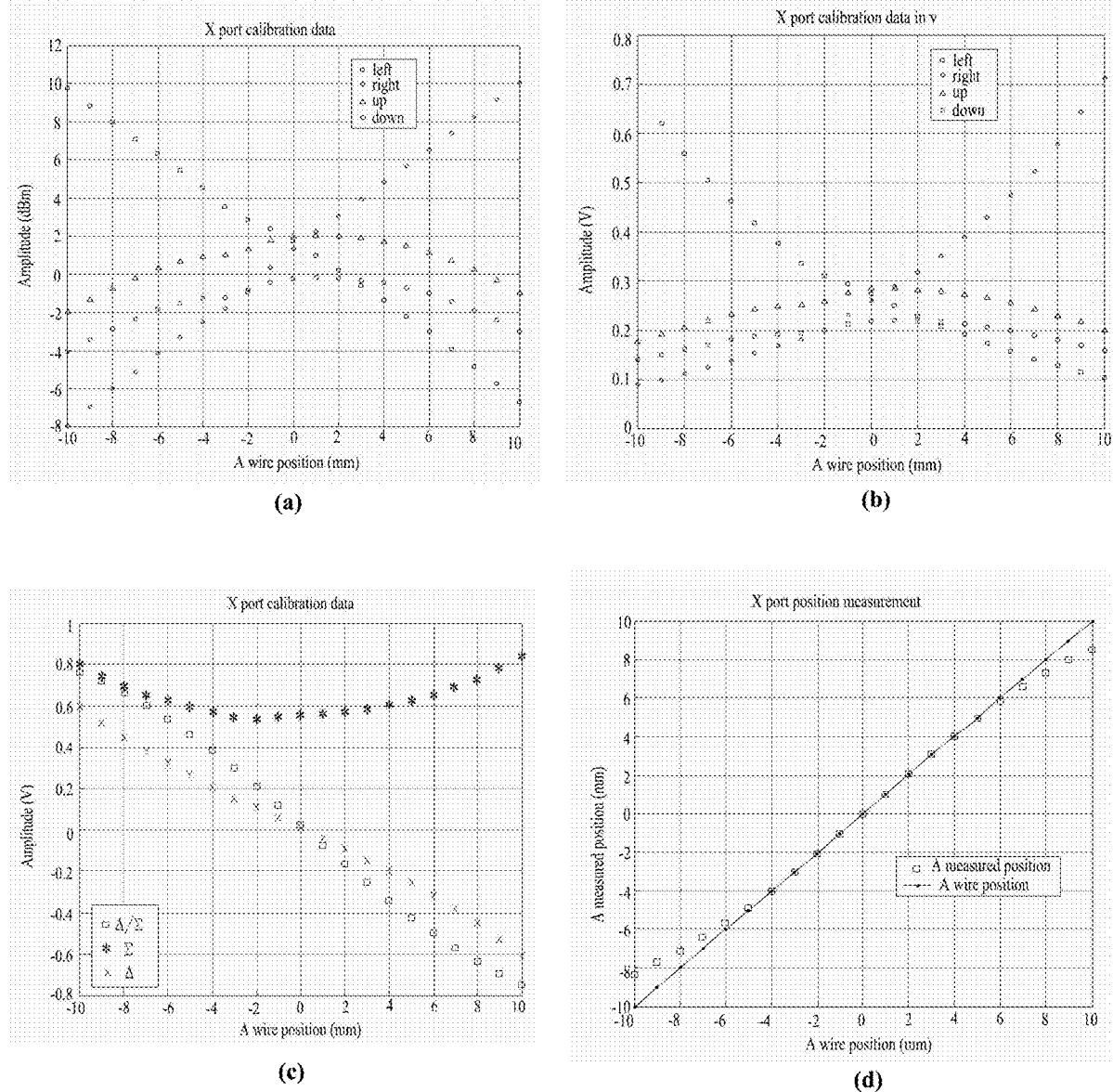
FIG. 5 is a diagram showing X-port calibration results and position measurement results using a $3^{rd}$ harmonic signal according to an embodiment of the present invention.

FIG. 5 is a diagram showing X-port calibration results and position measurement results using the $3^{rd}$ harmonic signal according to an embodiment of the present invention.

X-port calibration results and position using the $3^{rd}$ harmonic signal according to an embodiment of the present invention were measured as follows, and measurement results thereof are shown in FIG. 5.

Position resolution measurement of the $3^{rd}$ harmonic signal (243.75 MHz)

The frequency of a reference signal (LO) was fixed to 81.25 MHz

Measurement was performed based on signal intensity of 100 uA

Ground Readjustment of a Wire Test Bench

X-port Calibration slope: −0.0902 V/mm, offset: 0.0217 mm

X-port resolution limit=4.7 um

Figure 6:
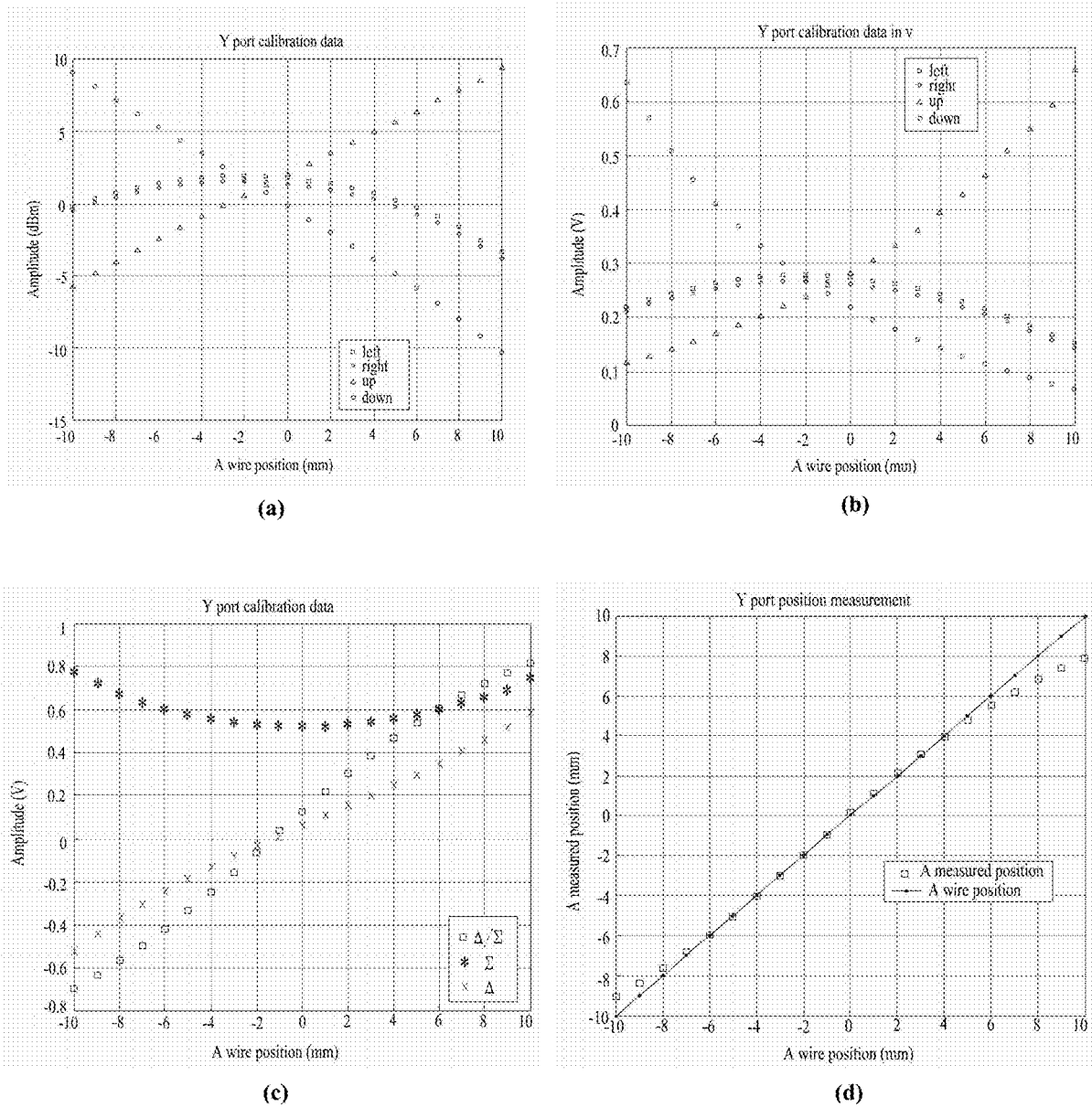
FIG. 6 is a diagram showing Y-port calibration results and position measurement results using a $3^{rd}$ harmonic signal according to an embodiment of the present invention.

X-port accuracy with narrow (±5 mm): 29.7 um, accuracy with full (±10 mm): 532.3 um FIG. 6 is a diagram showing Y-port calibration results and position measurement results using the 3rd harmonic signal according to an embodiment of the present invention.

Y-port calibration results and position using the $3^{rd}$ harmonic signal according to an embodiment of the present invention were measured as follows, and measurement results thereof are shown in FIG. 5.

Y-port Calibration slope: 0.0889 V/mm, offset: 0.1151 mm

Y-port resolution limit=5.6 um

Y-port accuracy with narrow (±5 mm): 57.9 um, accuracy with full (±10 mm): 592.7 um Position resolution measurement results using the $3^{rd}$ harmonic signal were measured 4.7 um in the horizontal direction and 5.6 um in the vertical direction. In the case of accuracy indicative of measurement accuracy of the position, measurement was performed on two cases as in the $1^{st}$ harmonics measurement. In a linear interval of +5 mm used to calculate a calibration slope, 29.7 um was measured in the horizontal direction and 57.9 um was measured in the vertical direction. In a ±10 mm interval, that is, the entire measurement interval, 532.3 um in the horizontal direction and 592.7 um in the vertical direction were measured as average values.

Figure 7:
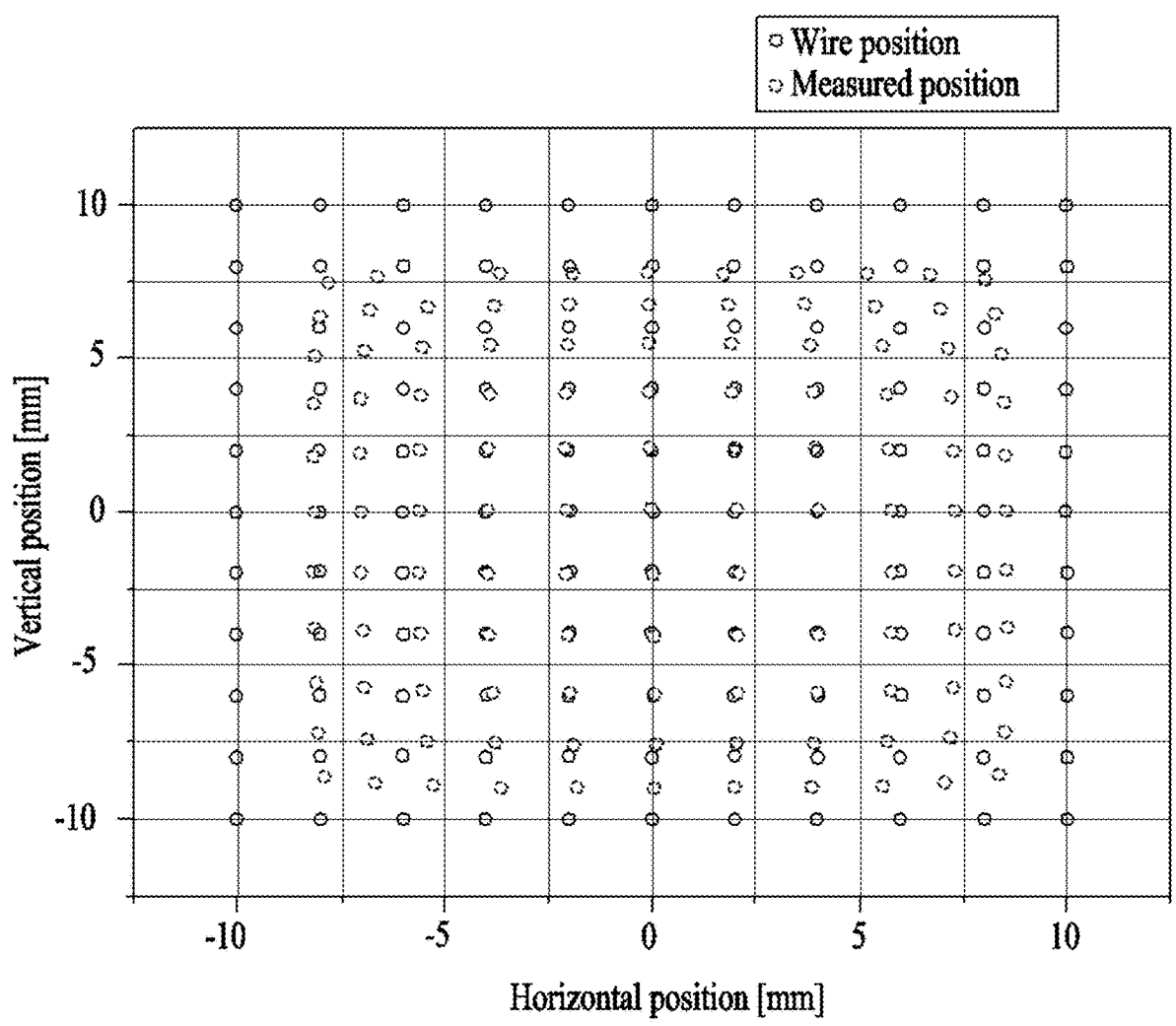
FIG. 7 is a diagram showing position mapping results using a $1^{st}$ harmonic signal according to an embodiment of the present invention.

FIG. 7 is a diagram showing position mapping results using the $1^{st}$ harmonic signal according to an embodiment of the present invention.

FIG. 7 shows the mapping results of button BPM measured while changing a wire position by 2 mm in the entire ±10 mm interval. It may be seen that accuracy is very high in the ±5 mm interval and a distortion phenomenon occurs in position measurement due to the limit of linear calibration near ±10 mm.

As describe above, it can be seen that the present invention can be used in a linear accelerator and a beam transmission line interval because the position resolution measurement results were measured much smaller than a limit value (100 um) permitted in a heavy ion accelerator interval.

Figure 8:
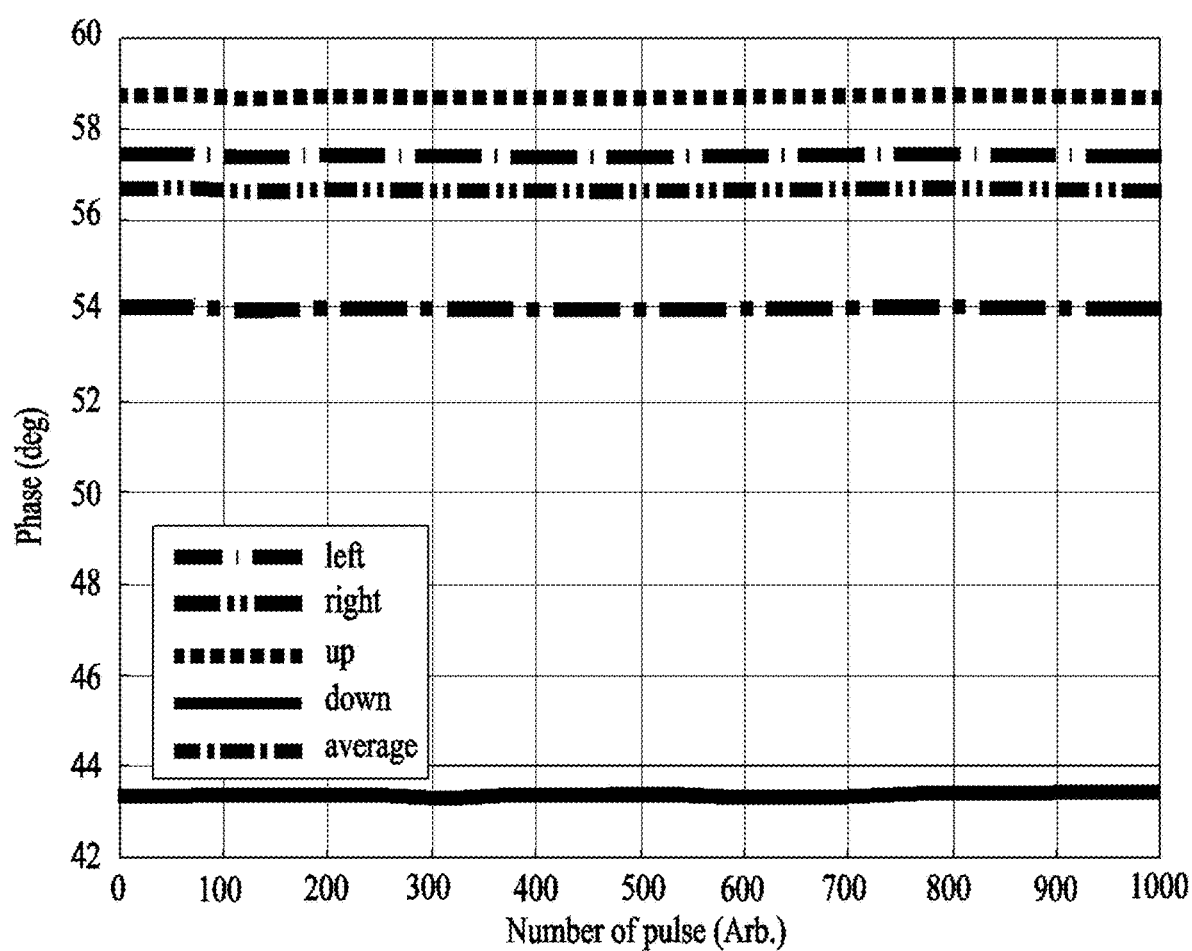
FIG. 8 is a diagram showing phase measurement results according to an embodiment of the present invention.

FIG. 8 is a diagram showing phase measurement results according to an embodiment of the present invention.

The button BPM may provide beam phase information using a signal read from four ports. This will be used for RF feedback. The signal processing system may measure a phase more precisely than limit measurement values suggested in the following table.

FIG. 8 shows phase measurement results measure using the button BPM. An average value was calculated using a total of 1000 beams. Phase information to be provided to RF feedback provides an average value of phase values measured in the four ports. Phase measurement resolution (e.g., 0.5 degree) during the 1000 pulse signals shows that measurement is performed precisely at a very small degree of 0.0278.

Figure 9:
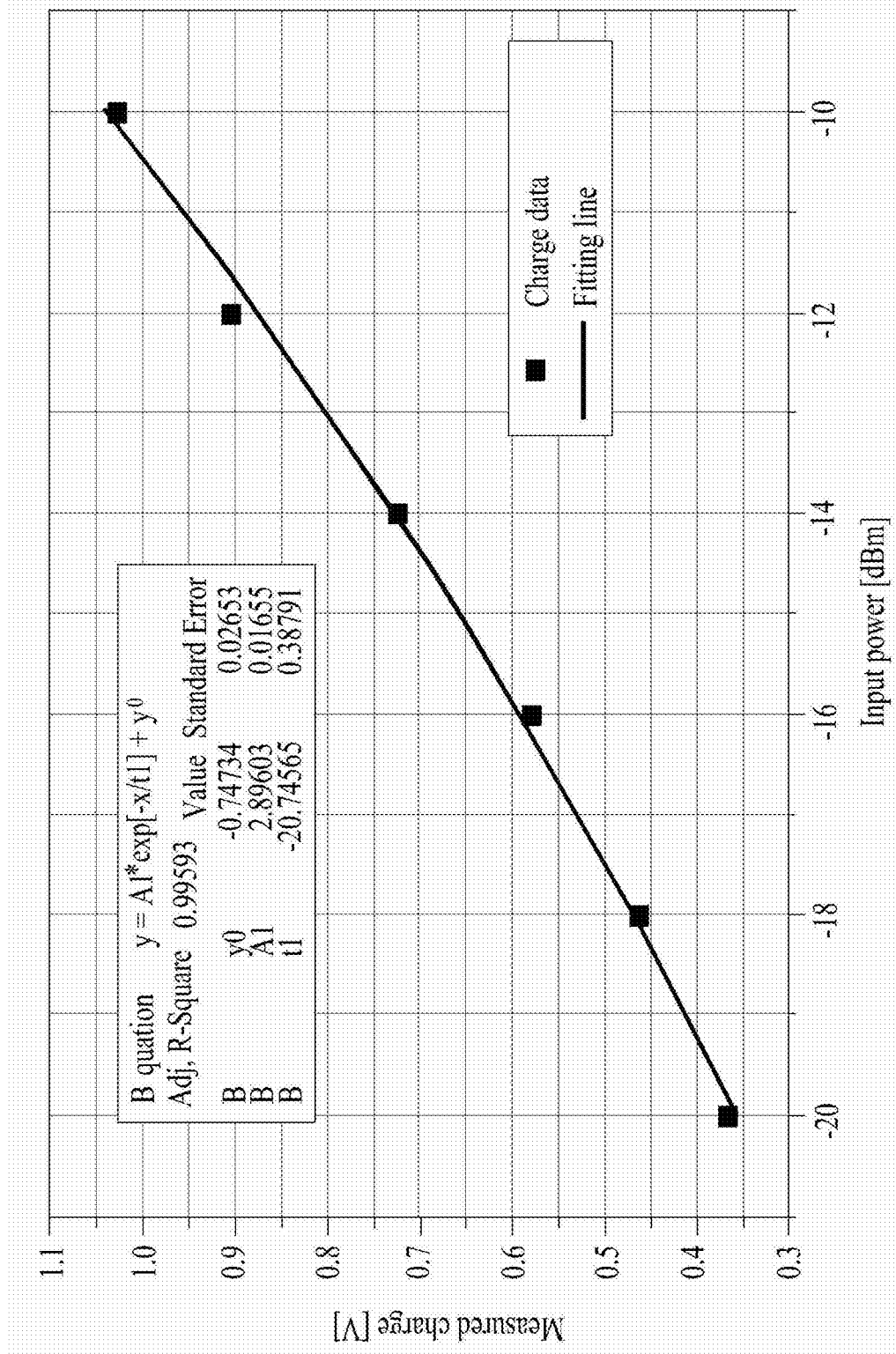
FIG. 9 is a diagram showing beam current results according to an embodiment of the present invention.

FIG. 9 is a diagram showing beam current results according to an embodiment of the present invention.

Additionally, the system for processing a signal of the beam position monitor includes logic capable of beam current information using the sum of four BPM output signals. Measurement was performed to calculate beam current information by measuring a change in an input signal versus a sum signal using a sum signal in the vertical direction and the horizontal direction. The measurement was performed by assuming a beam intensity change in a ±5 dBm interval based on −15 dBm, that is, the reference of the LO signal used for position resolution measurement. It was found that a change value of a voltage non-linearly changes depending on measurement results dBm.

The apparatus described above may be implemented in the form of a combination of hardware components, software components and/or hardware components and software components. For example, the apparatus and components described in the embodiments may be implemented using one or more general-purpose computers or special-purpose computers, for example, a processor, a controller, an arithmetic logic unit (ALU), a digital signal processor, a microcomputer, a field programmable array (FPA), a programmable logic unit (PLU), a microprocessor or any other device capable of executing or responding to an instruction. A processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary skill in the art may be aware that the processing device may include a plurality of processing elements and/or a plurality of types of processing elements. For example, the processing device may include a plurality of processors or a single processor and a single controller. Furthermore, other processing configuration, such as a parallel processor, is also possible.

Software may include a computer program, code, an instruction or one or more combinations of them and may configure the processing device so that it operates as desired or may instruct the processing device independently or collectively. Software and/or data may be interpreted by the processing device or may be embodied in a machine, component, physical device, virtual equipment or computer storage medium or device of any type or a transmitted signal wave permanently or temporarily in order to provide an instruction or data to the processing device. Software may be distributed to computer systems connected over a network and may be stored or executed in a distributed manner. Software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure solely or in combination. The program instruction recorded on the recording medium may have been specially designed and configured for the embodiment or may be known to those skilled in computer software. The computer-readable recording medium includes a hardware device specially configured to store and execute the program instruction, for example, magnetic media such as a hard disk, a floppy disk, and a magnetic tape, optical media such as CD-ROM or a DVD, magneto-optical media such as a floptical disk, ROM, RAM, or flash memory. Examples of the program instruction may include both machine-language code, such as code written by a compiler, and high-level language code executable by a computer using an interpreter.

In the method and system for processing a beam position monitor signal according to the embodiments of the present invention, the analog part can measure signal intensity of a very wide range using the RF switch and the dual LNA, and can measure a beam position signal of a 1ns pulse length at intervals of 1us using a fast ADC sampling frequency of 105 MHz. Furthermore, multiple harmonic signals are separated through digital down conversion to enable signal processing for each harmonics. Only an optimized harmonic signal of multiple harmonic signals, that is, characteristics of a heavy ion accelerator, is extracted through a digital band pass filter, and thus a beam position can be measured precisely. Furthermore, only a beam position is not simply measured, but beam position measurement, beam position measurement and relative beam current measurement, and a role as an assistant device of an accelerator device protection system can be performed using the digital circuit.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and the equivalents of the claims belong to the scope of the claims.

What is claimed is:

1. A system for processing a signal of a beam position monitor, the system comprising:
    an analog-to-digital converter (ADC) sampler configured to measure signal intensity through an optimization of an ADC sampling rate and bits using a radio frequency (RF) switch and a low noise amplifier (LNA) and to convert an analog signal into a digital signal; and
    an FPGA configured to perform digital signal processing, wherein the FPGA is further configured to comprise:
        a digital signal synthesizer configured to extract only an optimized harmonic signal of multiple harmonic signals of the digital signal converted by the ADC sampler through a digital band pass filter so that the multiple harmonic signals are separated and signal processing is performed for each harmonics; and
        an IQ calculator configured to perform beam position measurement, beam phase measurement and relative beam current measurement on the extracted digital signal through a digital circuit; and
    wherein the digital signal synthesizer is further configured to comprise:
        an averaging unit configured to perform averaging on a given interval of the digital signal converted by the ADC sampler;
        an A/P calculator configured to translate or inversely translate a size and phase using an IQ value calculated by an IQ calculator; and
        an FFT/filtering unit configured to perform a high-speed Fourier transform or filtering.

2. The system of claim 1, wherein the ADC sampler is further configured to comprise:
    the LNA configured to receive a pick-up RF signal and a reference RF signal and to amplify a monitor signal; and
    a low pass filter (LPF) configured to filter out noise of the RF signal.

3. The system of claim 1, wherein the digital signal synthesizer is further configured to perform signal processing using a $1^{st}$ harmonic signal of a predetermined frequency and a $3^{rd}$ harmonic signal of a predetermined frequency for a signal of a high-beta interval.

4. The system of claim 2, wherein the ADC sampler is further configured to:
    expand a measurable range of signal intensity using the RF switch and the LNA, and
    reduce a measurable interval of a beam position signal of a pulse length using a high-speed ADC sampling frequency of 105 MHz or more.

5. A method of processing a signal of a beam position monitor, the method comprising:
    measuring signal intensity through an optimization of an ADC sampling rate and bits using a radio frequency (RF) switch and a low noise amplifier (LNA) and converting an analog signal into a digital signal;
    extracting only an optimized harmonic signal of multiple harmonic signals of the digital signal converted by an analog-to-digital converter (ADC) sampler using a digital band pass filter so that the multiple harmonic signals are separated and signal processing is performed for each harmonics; and
    performing beam position measurement, beam phase measurement and relative beam current measurement on the extracted digital signal through a digital circuit,
    wherein the extracting comprises:
        performing averaging on a given interval of the digital signal converted by the ADC sampler;
        translating or inversely translating a size and phase using an IQ value calculated by an IQ calculator; and
        performing a high-speed Fourier transform or filtering.

6. The method of claim 5, wherein the measuring signal intensity through an optimization of an ADC sampling rate and bits using a radio frequency (RF) switch and a low noise amplifier (LNA) and converting an analog signal into a digital signal comprises:

receiving a pick-up RF signal and a reference RF signal, amplifying a monitor signal through the LNA, and filtering out noise of the RF signal through a low pass filter (LPF).

7. The method of claim 5, wherein the extracting comprises:

performing, by an averaging unit, averaging on the given interval of the digital signal converted by the ADC sampler, translating or inversely translating, by an A/P calculator, the size and phase using the IQ value calculated by the IQ calculator; and performing, by an FFT/filtering unit, the high-speed Fourier transform or filtering.

8. The method of claim 5, wherein the signal processing is performed using a $1^{st}$ harmonic signal of a predetermined frequency and a $3^{rd}$ harmonic signal of a predetermined frequency for a signal of a high-beta interval.

9. The method of claim 6, wherein:

a measurable range of signal intensity is expanded using the RF switch and the LNA, and a measurable interval of a beam position signal of a pulse length is reduced using a high-speed ADC sampling frequency of 105 MHz or more.

\* \* \* \* \*